United States Patent
Song et al.

(10) Patent No.: US 9,254,140 B2
(45) Date of Patent: Feb. 9, 2016

(54) SINGLE PROBE WITH DISTURBER

(76) Inventors: Tao Song, Erie, PA (US); Shu Du, Erie, PA (US)

(*) Notice: Subject to any disclaimer, the term of this patent is extended or adjusted under 35 U.S.C. 154(b) by 1122 days.

(21) Appl. No.: 12/657,248

(22) Filed: Jan. 15, 2010

(65) Prior Publication Data

US 2010/0274269 A1    Oct. 28, 2010

(51) Int. Cl.
*A61B 17/22* (2006.01)
*A61B 17/3207* (2006.01)

(52) U.S. Cl.
CPC ....... *A61B 17/22012* (2013.01); *A61B 17/3207* (2013.01)

(58) Field of Classification Search
CPC .............. A61B 17/22012; A61B 17/3207; A61B 17/22004; H04B 3/56
USPC .......................................... 606/128, 159, 163
See application file for complete search history.

(56) References Cited

U.S. PATENT DOCUMENTS

| | | | | |
|---|---|---|---|---|
| 4,311,145 A * | 1/1982 | Esty et al. | | 606/42 |
| 4,979,952 A * | 12/1990 | Kubota et al. | | 606/169 |
| 5,879,314 A | 3/1999 | Peterson et al. | | |
| 6,558,397 B2 * | 5/2003 | Hirt et al. | | 606/128 |
| 6,875,220 B2 * | 4/2005 | Du et al. | | 606/169 |
| 6,942,677 B2 * | 9/2005 | Nita et al. | | 606/169 |
| 7,387,612 B2 | 6/2008 | Pal et al. | | |
| 2002/0010478 A1 * | 1/2002 | Menne et al. | | 606/128 |
| 2002/0010486 A1 * | 1/2002 | Hirt | | 606/169 |
| 2004/0010267 A1 * | 1/2004 | Nakamura et al. | | 606/128 |
| 2005/0209620 A1 | 9/2005 | Du et al. | | |
| 2007/0066978 A1 * | 3/2007 | Schafer et al. | | 606/128 |
| 2007/0162050 A1 * | 7/2007 | Sartor | | 606/128 |
| 2008/0061784 A1 | 3/2008 | Pal et al. | | |

FOREIGN PATENT DOCUMENTS

| | | |
|---|---|---|
| EP | 0353294 B1 | 8/2000 |
| EP | 0722295 B1 | 4/2003 |

* cited by examiner

*Primary Examiner* — Thomas McEvoy
*Assistant Examiner* — Julie A Szpira

(57) ABSTRACT

A single probe percutaneous surgical instrument for de-bulking/removing thrombus/clog/calculi has an actuator assembly (4), a probe set (13), an operating switch (10), and a generator (12). The actuator assembly (4) has a proximal end (4a) and a distal end (4b), a cable connector (1), a suction connector (2), and actuator switch (3) mounted with the proximal end (4a) and a horn (5) mounted at the distal end (4b). The probe set (13) is mounted to the horn (5) and includes at least one disturber (6), a spring (7), a spring adjusting nut (8) and a fixed probe (9), the cable connector (1) connecting to the generator (12) through a cable, and the suction connector (2) connecting to a suction system. The actuator switch (3) controls a probe vibration mode through the generator (12), the actuator assembly (4) comprising at least two piezoelectric ceramic rings (18) assembled with a bolt (15), the horn (5) and a back plated (16). The horn (5) is mounted on the distal end (4b) of the actuator assembly (4), the horn (5) being coupled with the bolt (15) and the piezoelectric rings (18), the at least one disturber (6) and the spring (7) being mounted on the fixed probe (9) using the spring adjusting nut (8). The generator (12) includes a microprocessor and the microprocessor is programmed to control the actuator vibration mode, the fixed probe optimal vibration frequency and the disturbing strength of the disturbers.

3 Claims, 2 Drawing Sheets

SINGLE PROBE WITH DISTURBER

CROSS-REFERENCE TO RELATED APPLICATIONS

This application claims priority from Chinese patent application Ser. No. 200910136077.0, filed Apr. 27, 2009.

TECHNICAL FIELD

The present invention is generally directed to a surgical instrument for disintegrating/removing thrombus, clog and calculi. It is more particularly directed to percutaneous surgical instruments for use in cardiac, blood vessel surgical application and endoscopic procedures.

BACKGROUND ART

Fixed ultrasonic probe devices that operate in the frequencies 20-30 kHz range are best in disintegrating thrombus and clog using cavitations. It is known that sweeping around resonant frequency introduces a disturbance which gives even better performance for disintegration. This invention will have additional low frequency mechanical disturbance.

DISCLOSURE OF INVENTION

It is object of the invention to enhance the application of ultrasound in the treatment of thrombi and clogs or clots.

It is another object of the invention to improve ultrasound treatment of thrombi and other obstructions.

These objects are accomplished, in one aspect of the invention, by the provision of a single, fixed probe that utilizes vibration disturbers. In another aspect of the invention, the object are accomplished by the provision of a percutaneous surgical instrument for de-bulking/removing thrombus/clog/calculi comprising: an actuator assembly, a probe set, an operating switch, and a generator, the actuator assembly having a proximal end and a distal end, a cable connector, a suction connector, and actuator switch mounted with the proximal end and a horn mounted at the distal end; the probe set being mounted to the horn and including at least one disturber, a spring, a spring adjusting nut and a fixed probe, the cable connector connecting to the generator through a cable, the suction connecting to a suction system; the actuator switch controlling a probe vibration mode through the generator, the actuator assembly comprising: at least two piezoelectric ceramic rings assembled with a bolt, the horn and a back plate; the horn being mounted on the distal end of the actuator assembly, the horn being coupled with the bolt and the piezoelectric rings, the at least one disturber and the spring being mounted on the fixed probe using the spring adjusting nut, the generator including a microprocessor and the microprocessor being programmed to control the actuator vibration mode, the fixed probe optimal vibration frequency and the disturbing strength of the disturbers.

The use and application of the disturbers increases the efficacy of instrument. Further, the use of the vibrational disturbers allows a single probe to be used for small work channel scope operations in cardiac and blood vessel surgical applications as well as other endoscopy procedures.

BEST MODE FOR CARRYING OUT THE INVENTION

For a better understanding of the present invention, together with other and further objects, advantages and capabilities thereof, reference is made to the following disclosure and appended claims taken in conjunction with the above-described drawings.

Figure 1:
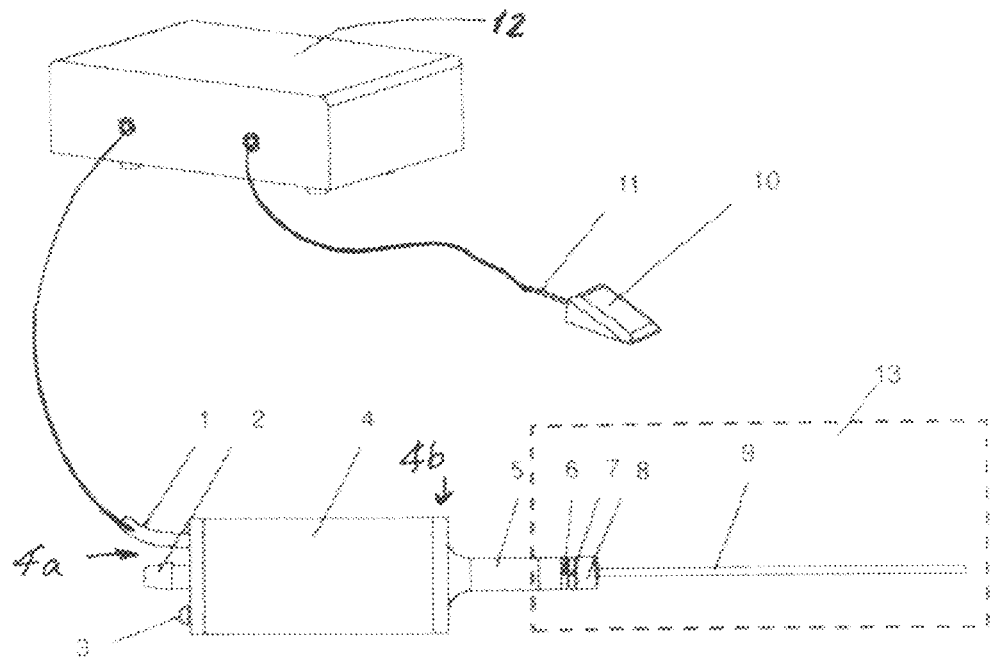
FIG. 1 is a diagrammatic view, in perspective, of an aspect of the invention.
Figure 2:
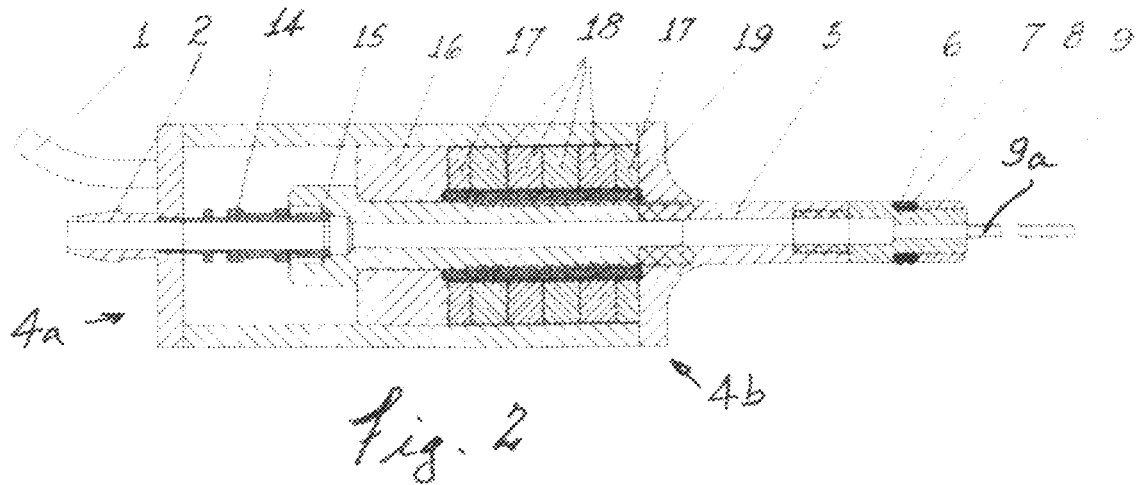
FIG. 2 is an elevation, sectional view of an actuator in accordance with an aspect of the invention.
Figure 3:
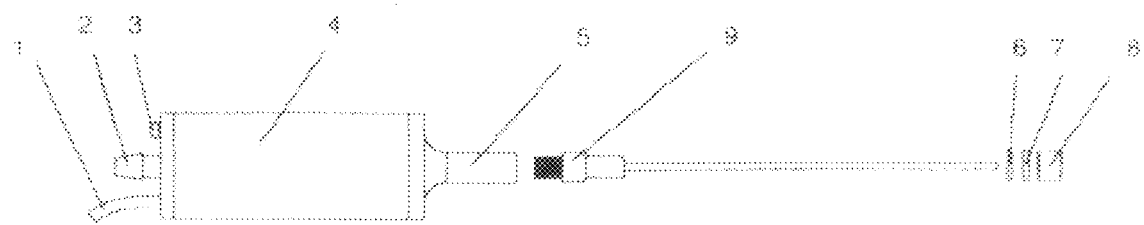
FIG. 3 is an exploded view of an embodiment of the invention.
Figure 4:
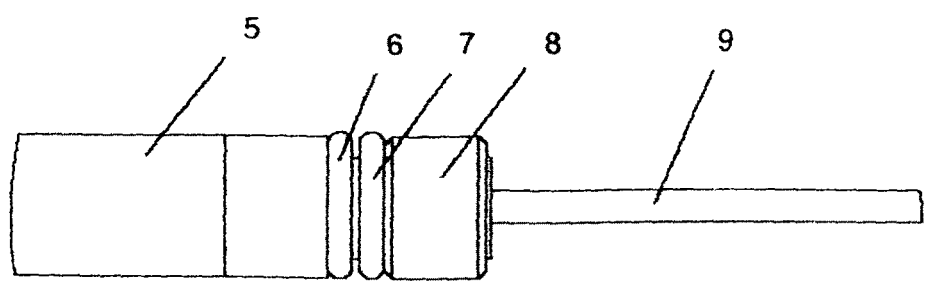
FIG. 4 is an enlarged view of the distal end of the instrument illustrating a disturber in a position to move to contact a second disturber or spring.

Referring now to the drawings with greater particularity, there is shown in FIG. 1 a percutaneous surgical instrument for disintegrating/removing thrombus, clog and calculi. The instrument includes generally an actuator 4, a probe set 13, a switch for controlling the operation, which can be a foot-switch 10 and a power supply such as a generator 12.

The actuator 4 has a cable connector 1 that connects to the generator 12, a suction connector 2, which can connect to a supply of suction, not shown, an actuator switch 3 preferably attached to the proximal end 4a of the actuator 4 and the horn 5. The probe set 13 includes the disturbers 6, the spring 7, the adjusting nut 8 and the fixed probe 9.

The actuator body 4 comprises at least 2 piezoelectric crystals 18, that can be ceramic rings, that are assembled with the bolt 15, the horn 5 and the back plate 16. The bolt 15 applies pre-stress on the piezoelectric ceramic crystal rings 18. The function of the actuator 4 is to transfer the electric energy from the generator 12 to the mechanical vibration energy.

The horn 5 is positioned on the distal end 4b of the actuator 4 and is coupled with the bolt 15 and the piezoelectric rings 18 to amplify the vibration of the rings 18. The disturbers 6 are mounted on the horn 5 and contribute additional vibration frequency. The amplitude and frequency of this additional vibration is dependent on the movement of the disturbers where the movement is controlled by the adjusting nut position. Introducing disturbance to such a system can generate a desired overshoot if it can be controlled properly. This property of controlled overshoot can generate strong impulses from the force to the probe. A controlled driving signal from the generator, in combination with the nut position between the disturbers, adjusts the impact to the thrombus, clog and calculi thru the probe.

The disturber 6, which can be more than one, and including the spring 7, are mounted on the probe 9 for disturbing the ultrasonic vibration to increase the de-bulking rate or removing rate. The adjusting nut 8 is used for changing the disturbing frequencies in accordance with the nut position on the probe.

In a preferred embodiment of the invention, the disturbers are stainless steel rings and there at least two of them.

The fixed probe 9 can include a lumen 9a when suction is applicable, or it can be a simple, solid wire in those cases in which suction is not necessary, Generally, the disturbers are driven by the generator 12 through the actuator 4 and the fixed probe 9 with various frequencies, pulse cycle frequencies and duty cycles to maximize the efficiency of the thrombi break-up.

The size of the disturbers may be varied in use for different driven frequencies and maximizing the disturbing frequencies to breakup and/or remove the thrombi/clog/calculi.

While there have been shown and described what are at present considered to be the preferred embodiments of the invention, it will be apparent to those skilled in the art that various changes and modifications can be made herein without departing from the scope of the invention as defined by the appended claims.

What is claimed is:

1. A single probe percutaneous surgical instrument for de-bulking/removing thrombus/clog/calculi comprising:
    an actuator assembly (4), a probe set (13), an operating switch (10), and a generator (12), said actuator assembly (4) having a proximal end (4*a*) and a distal end (4*b*), a cable connector (1), a suction connector (2), and actuator switch (3) mounted with said proximal end (4*a*) and a horn (5) mounted at said distal end (4*b*);
    said probe set (13) being mounted to said horn (5) and including at least one disturber (6), a spring (7), a spring adjusting nut (8) and a fixed probe (9), said cable connector (1) connecting to said generator (12) through a cable, said suction connector (2) connecting to a suction system;
    said actuator switch (3) controlling a probe vibration mode through the generator (12), said actuator assembly (4) comprising:
    at least two piezoelectric ceramic rings (18) assembled with a bolt (15), the horn (5) and a back plated (16); said horn (5) being mounted on the distal end (4*b*) of said actuator assembly (4), said horn (5) being coupled with said bolt (15) and said piezoelectric rings (18), said at least one disturber (6) and said spring (7) being mounted on said fixed probe (9) using said spring adjusting nut (8), said generator (12) including a microprocessor and said microprocessor being programmed to control said actuator vibration mode, said fixed probe optimal vibration frequency and the disturbing strength of said disturbers.

2. The single probe percutaneous surgical instrument according to claim 1 wherein said fixed probe (9) includes a lumen (9*a*) therethrough for aspiration of disintegrated thrombus/clog/calculi.

3. The single probe percutaneous surgical instrument according to claim 1 wherein said fixed probe (9) is a wire for disintegrating thrombus/clog/calculi where removing said thrombus/clog/calculi is not necessary.

* * * * *